(12) United States Patent
Yu et al.

(10) Patent No.: US 9,272,102 B1
(45) Date of Patent: Mar. 1, 2016

(54) MEDICINE BOX COUNTER

(71) Applicant: National Applied Research Laboratories, Taipei (TW)

(72) Inventors: Chih-Sheng Yu, Hsinchu (TW);
Yu-Cheng Ou, Hsinchu (TW);
Fan-Chun Hsieh, Hsinchu (TW);
Ping-Hung Lin, Hsinchu (TW);
Shui-Jung Chen, Hsinchu (TW);
Jiann-Shiun Kao, Hsinchu (TW);
Shu-Hui Hung, Hsinchu (TW)

(73) Assignee: NATIONAL APPLIED RESEARCH LABORATORIES, Taipei (TW)

( * ) Notice: Subject to any disclaimer, the term of this patent is extended or adjusted under 35 U.S.C. 154(b) by 1 day.

(21) Appl. No.: 14/451,642

(22) Filed: Aug. 5, 2014

(51) Int. Cl.
*A61M 11/00* (2006.01)
*G06M 3/02* (2006.01)
*A61M 15/00* (2006.01)
*B65D 25/54* (2006.01)

(52) U.S. Cl.
CPC ....... *A61M 15/0071* (2014.02); *A61M 15/0021* (2014.02); *B65D 25/54* (2013.01)

(58) Field of Classification Search
USPC ...................... 235/132; 128/200.23
See application file for complete search history.

(56) References Cited

U.S. PATENT DOCUMENTS

| | | | | |
|---|---|---|---|---|
| 2011/0265788 | A1* | 11/2011 | Wu ...................... | A61M 15/008 128/200.23 |
| 2011/0283997 | A1* | 11/2011 | Walsh ............... | A61M 15/0065 128/200.23 |

* cited by examiner

*Primary Examiner* — Daniel Hess
(74) *Attorney, Agent, or Firm* — Jackson IPG PLLC; Demian K. Jackson

(57) ABSTRACT

Disclosed is a medicine box counter, which comprise a case body, comprising a bottom seat, an upper cap movably combined with the case body, and a plurality of resilient elements disposed between the bottom seat and the upper cap. As such, the medicine and the bottom seat are directly combined so that when the user exerts a pressure upon the upper cap in the use course, the resilient elements may be indirectly extruded and thus the bottom seat triggers the count mechanism to count, and after the pressure on the upper cap is released, the upper cap automatically restores to its original position by means of the resilient elements, whereby achieving the efficacies of rapid assembly, convenient use, effective medicine-taken count and reduced manufacturing cost are provided.

5 Claims, 6 Drawing Sheets

MEDICINE BOX COUNTER

FIELD OF THE INVENTION

The present invention pertains to a medicine box counter, and particularly to a medicine box counter possessing the efficacies of rapid assembly, convenient use, efficient medicine use counting and reduced manufacturing cost.

DESCRIPTION OF THE RELATED ART

With the environmental changes brought about from the green house effect, human respiratory is adversely affected, increasing the occurrence of some lung diseases, such as asthma. Aside from the environmental factors, asthma may be inherited. This disease has the features of trachea inflammation, trachea hypersensitive reaction, and reversible trachea contraction. An efficient way to cure asthma is conducted by inhaling. Over the decades, a lot of inhalator designs have been brought onto the market, enabling the asthma patients to inhale medicine to control discomfort brought from asthma. The medicine inhaling manner may have the main advantages of (1) directing the medicine to respiratory organs such as trachea, bronchus and lung, where medicine is generally harder to reach, and (2) fewer side effects as compared to injection and oral medicine.

Inhaling medicine for asthma may typically be classified into four, beta-2 agonist, inhaling Anticholinergic agents, and inhaling steroid and non-steroid anti-inflammatory drugs. Inhaling medicine devices may be classified into metered-dose inhaler (MDI), dry powder inhaler (DPI), and neulizer.

In the MDI, the associated components are disposed within a small steel cylinder, including medicine, coolant, and surface-active agent. When the steel bottle is pressed, the coolant exerts to atomize the medicine into minute particles and the particles flows into the human lungs, which then soothes the symptoms. However, the pressing force needs to be large enough to set the medicine within the steel bottle off, imposing a challenge to small children.

The DPI is operated by inhaling the powder form of medicine into the lungs through a sucker by the asthma patient. However, the DPI requires even a small child to have a relatively large inhaling force. The DPI has the same medical efficacy as the MDI, but a different inhaling manner. The DPI is easier to inhale but requires a larger inhaling force, and this generally places an age limitation on the user, such as children under the age of five. And this limitation case may be similarly applied onto those asthma patients in a considerably deteriorated state. The DPI is administered without using a chlorine fluorine compound (CFC) and thus is somewhat environmentally friendly. However, it still has the issue of poor storage capability in a humid climate.

For those patients with difficultly using the MPI and DPI, the nebulizer provides another good choice, which employs ultrasound wave technology to atomize the medicine first and then let the asthma patient inhale. However, this involves a more complicated device.

In a comparative sense, the MPI has the advantages of simple operation and high portability, but no exact indication as to how many times to have the asthma patient inhale the medicine. This indication may be very crucial as the patient may have an issue if the medicine is inhaled too many times.

In response to this consideration, the US patent, U.S. Pat. No. 5,421,482 disclosed a technology for indicating if the medicine is full by using a gear driving a relative movement of driver pawls, in which a rotary effect is caused when the medicine bottle is pressed, bringing an indicia to move with respect to an outer cover. When the indicia or the outer cover moves to the same mark, a selector is positioned at a place other than the indicia and the outer mask. In this manner, when the selector is set as being "empty" or "full", an indication regarding if the medicine inhaling device is full or not may be obtained.

In addition, the US patent, U.S. Pat. No. 8,215,299 disclosed an MPI spray counter, in which a dose counter is separate from a medication canister, so that the triggering number for the medicine may be clearly pointed out and the case may be preserved where medicine in the medication canister is insufficient and reused when another kind of medicine is newly applied. When an upper cap is pressed and thus a contact between an increment button on the upper cap and a projection exceeds a threshold time ($0.01s \leq T_{crit} < 0.5s$), an effective trigger is valid. However, in the process of pressing, the resilient force of the spring may cause inconvenience for the user and a converter needs to be replaced in the case of medication canister of different bottle body size being used.

In addition, some commonly used MIPs, such as DOSER made from Puff Minder, are characterized in that the counter reversely counts upon being pressed and the user is warned of empty when the counts show "zero", and a reset function is also provided. Another example is flutiform made form Aptar Pharma company, in which not only the adverse count function is provided but also the user may be informed of if the device is empty by showing color and number value. However, these mechanical or electronic MPIs have the disadvantage of excessive volume, inconvenient pressing and accidental discharge, resulting in more difficult use.

In view of the shortcomings encountered in the prior art, the inventors of this application provides a medicine box counter to solve many of the longstanding issues in the related art.

SUMMARY OF THE INVENTION

It is an object of the present invention to provide a medicine box counter, in which a medicine and a bottom seat are directly combined so that when a user exerts a pressure upon an upper cap in the course of use, resilient elements may be indirectly extruded and thus the bottom seat triggers a count mechanism to count, and after the pressure on the upper cap is released, the upper cap automatically restores to its original position by means of the resilient elements, and thus the efficacies of rapid assembly, convenient use, effective medicine-taken count and reduced manufacturing cost are achieved.

To achieve the object of the present invention, the medicine box counter comprises a case body, comprising a bottom seat, an upper cap movably combined with the case body, and a plurality of resilient elements disposed between the bottom seat and the upper cap; and a count mechanism, disposed between the bottom seat and the upper cap, drivable by a compression course between the upper cap and the bottom seat to count, the compression force between the upper cap and bottom seat being recoverable to an original course by the plurality of resilient elements.

In an embodiment, the bottom seat has a first face having a protruding rod disposed thereon and movably contacting the count mechanism and a second face having a first sleeved area and a second sleeved area communicatively connected to each other and having a step difference therebetween.

In an embodiment, the first and second sleeved areas each have an inner rim having a plurality of lean-against portions disposed thereon.

In an embodiment, the upper cap has a first face having a window hole thereon and a second face having a transparent cap plate enclosed thereon, and a through hole corresponding to the count mechanism is disposed at a position neighboring to the window hole.

In an embodiment, the count mechanism comprises a fixation seat, a count unit fixed on the fixation seat and having a first face and a second face, a first triggering element disposed on the first face of the count unit, a second triggering unit disposed on the second face of the count unit and corresponding to the protruding rod, a pressing button corresponding to the protruding hole and the first triggering element, a displaying unit connected to the count unit and corresponding to the window hole, and a power unit connected to the count unit, wherein the resilient elements are disposed between the bottom seat and the fixation seat.

In an embodiment, each of the resilient elements is made of one of silicon glue and polydimethylsiloxane (PDMS).

BRIEF DESCRIPTIONS OF THE DRAWINGS

DESCRIPTION OF THE PREFERRED EMBODIMENTS

Figure 1:
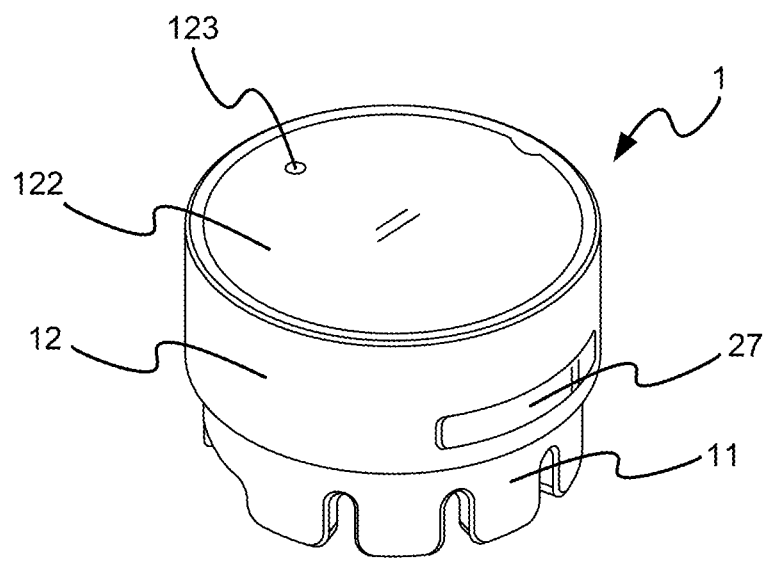
FIG. 1 is a schematic diagram of an outlook according to the present invention.
Figure 2:
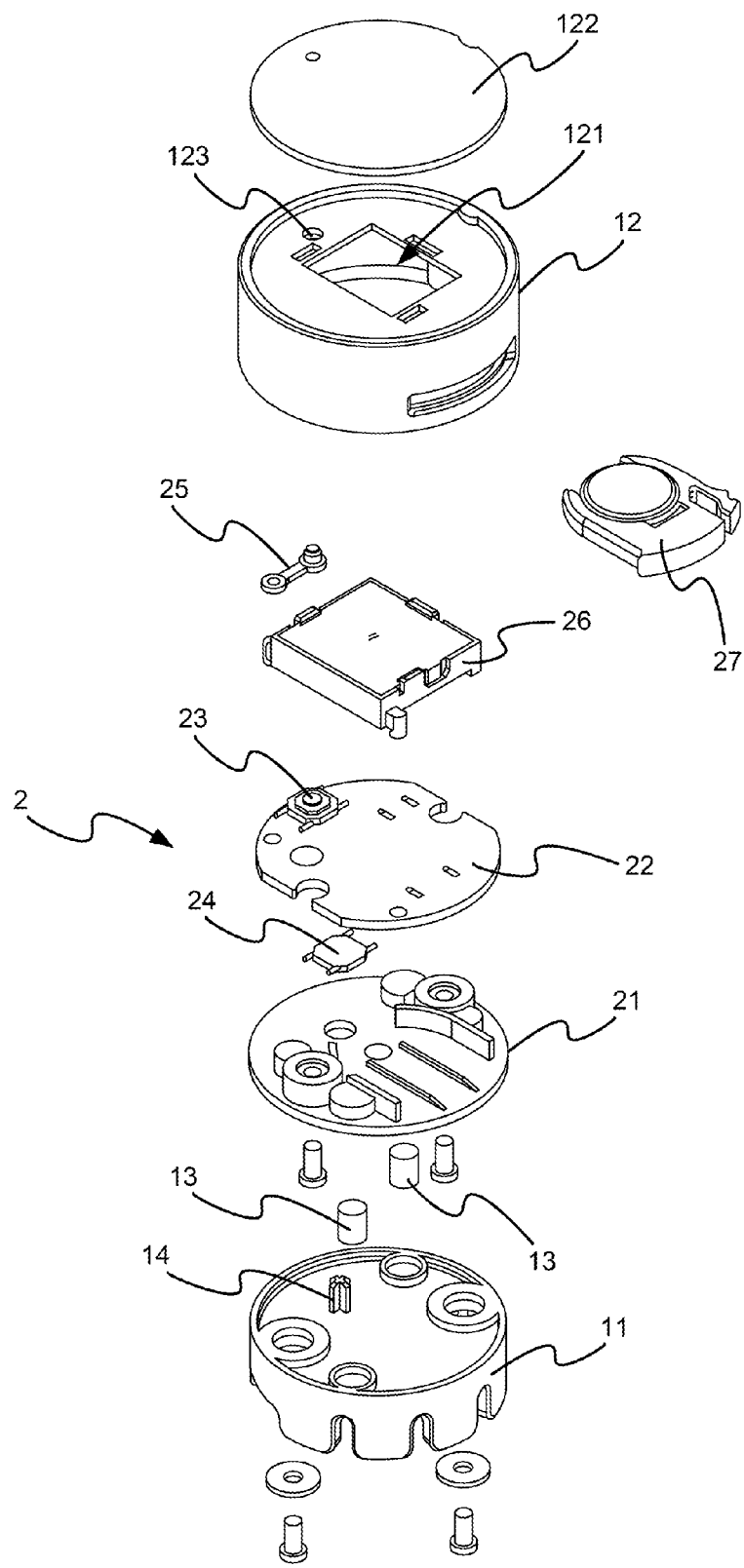
FIG. 2 is an exploded schematic diagram of the present invention.
Figure 3:
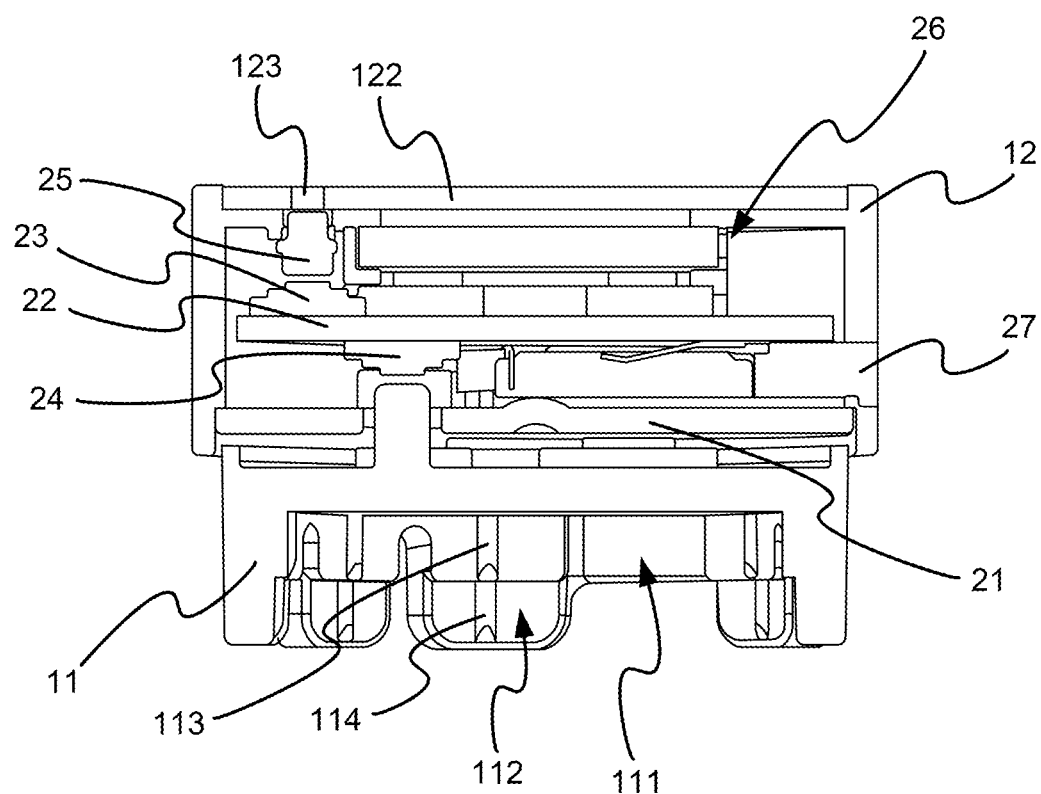
FIG. 3 is a schematic diagram of a cross sectional state according to the present invention.
Figure 4:
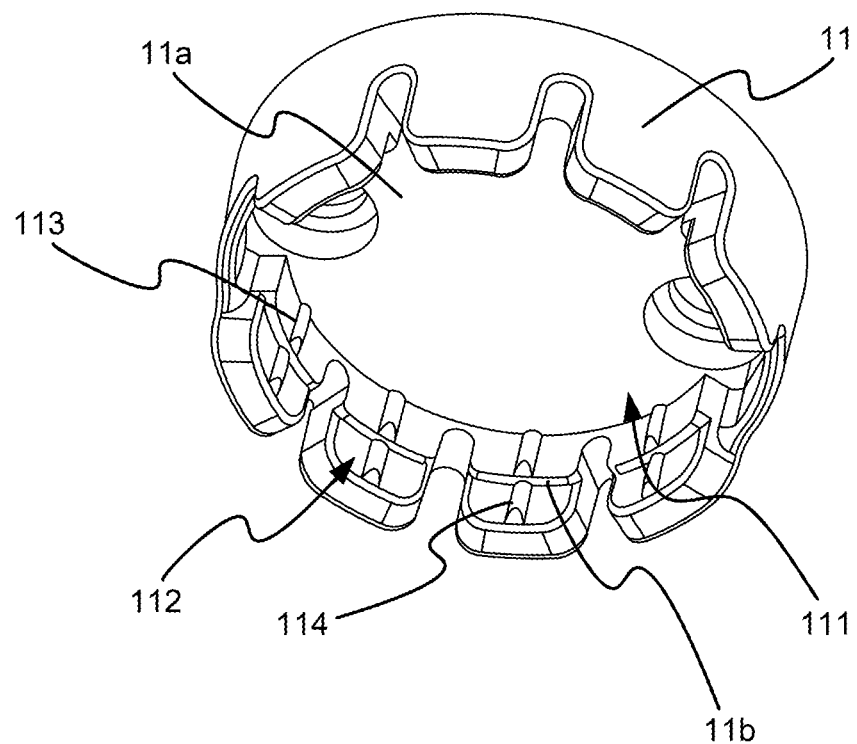
FIG. 4 is a schematic diagram of an upward view according to the present invention.

Referring to FIG. 1, FIG. 2, FIG. 3 and FIG. 4, which are a schematic diagram of an outlook according to the present invention, an exploded schematic diagram of the present invention, a schematic diagram of a cross sectional state according to the present invention, and a schematic diagram of an upward view according to the present invention, respectively. As shown, the medicine box counter comprises a case body 1 and a count mechanism 2.

The case body 1 comprises a bottom seat 11, an upper cap 12, and resilient elements 13. The upper cap 12 is movably combined with the case body 11. The resilient elements 13 are disposed between the bottom seat 11 and the upper cap 12. The bottom seat 11 has a first face having a protruding rod 14 disposed thereon. The protruding rod 14 is electrically conductive and drives a second triggering element, as will be described below, to operate. The bottom seat 11 further has a first sleeved area 111 and a second sleeved area 112 communicatively connected to each other and having a step difference there between. The first and second sleeved areas 111, 112 each have an inner rim having a plurality of lean-against portions 113, 114 disposed thereon. The upper cap 12 has a window hole 121 on its one face thereon. The window hole 121 is enclosed by a transparent cap plate 122 at its one face. A through hole 123 is disposed at a position neighboring to the window hole 121.

In addition, each of the resilient elements is made of silicon glue or polydimethylsiloxane (PDMS), which has a hardness which may be adjustable by changing its proportion of components.

The count mechanism 2 is disposed between the bottom seat 11 and the upper cap 12 and may be drivable by a compression course between the upper cap 12 and the bottom seat 11 to count. The original course of the upper cap 12 and bottom seat 11 may be recovered by the resilient elements 13.

The count mechanism 2 comprises a fixation seat 21, a count unit 22, a first triggering element 23, the second triggering unit 24 having been mentioned above, a pressing button 25, a displaying unit 26, and a power unit 27. Between the resilient elements 13, the bottom seat 11 and the fixation seat 21. The count unit 22 is fixed on the fixation seat 21. The first triggering element 23 is disposed on one face of the count unit 22. The second triggering unit 24 is disposed on the other face of the count unit 22 and corresponding to the protruding rod 14. The pressing button 25 is disposed corresponding to the protruding hole 123 and the first triggering element 23. The displaying unit 26 is connected to the count unit 22 and disposed corresponding to the window hole 121. The power unit 27 is connected to the count unit 22.

Figure 5:
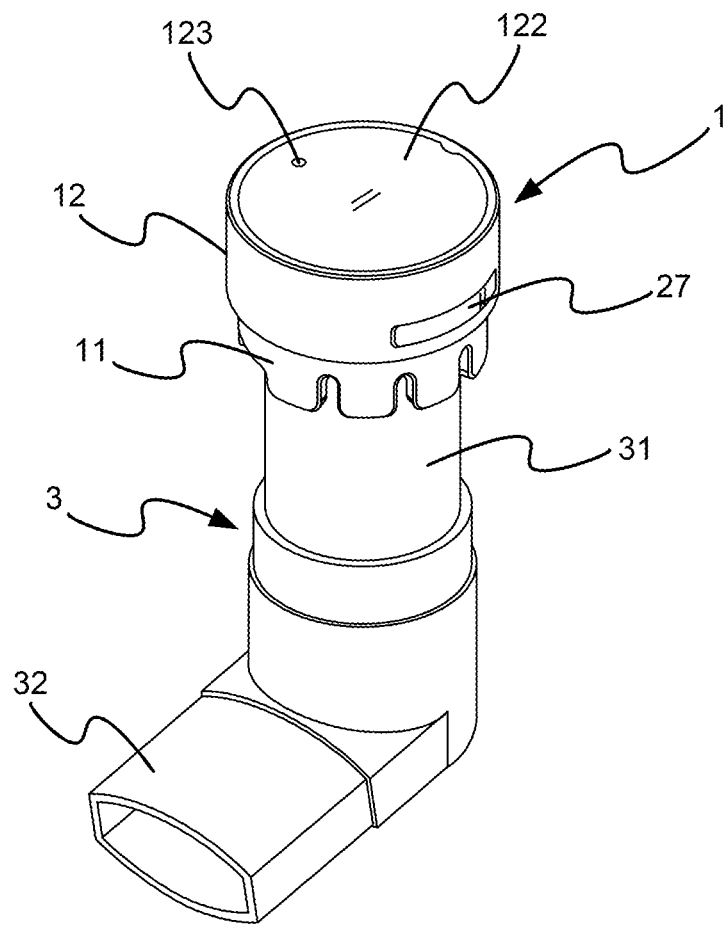
FIG. 5 is a schematic diagram showing a use according to the present invention.
Figure 6:
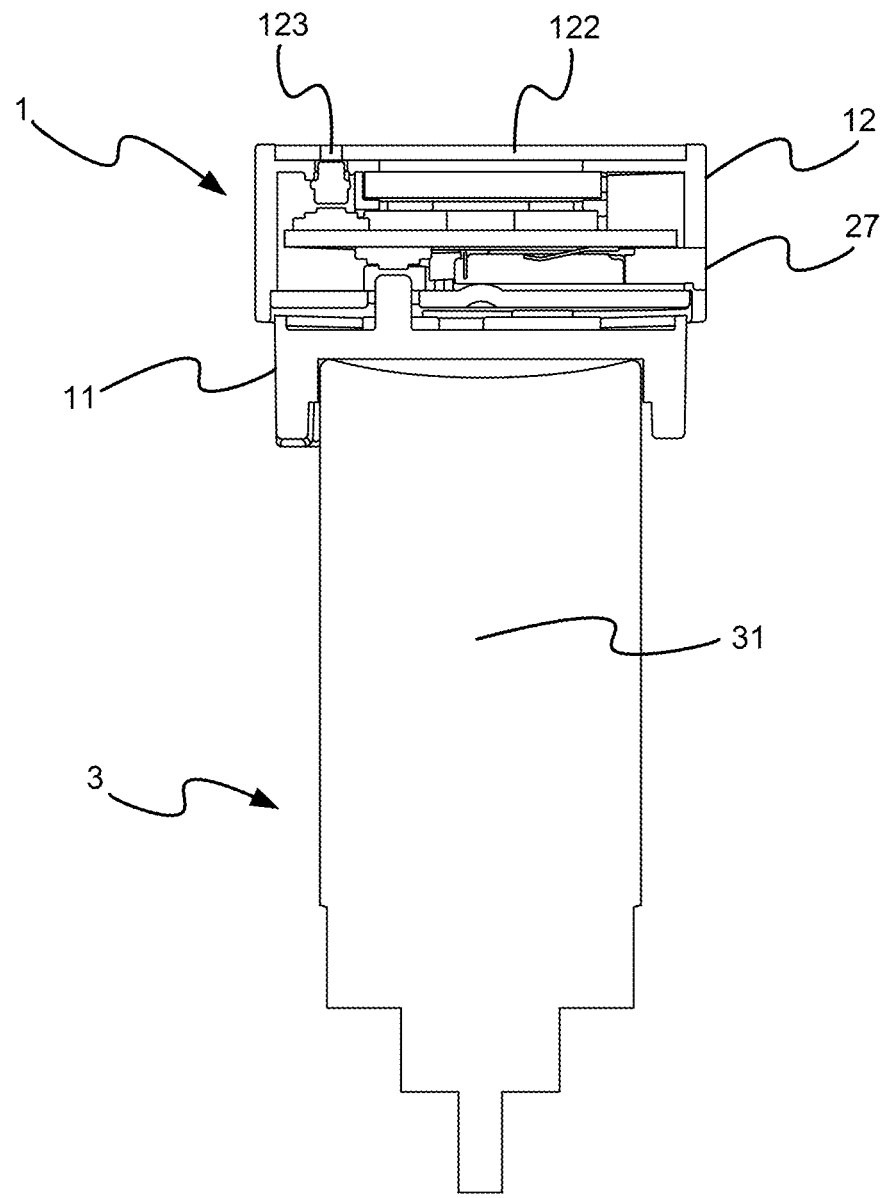
FIG. 6 is a cross sectional schematic diagram showing a use state according to the present invention.

Referring to FIG. 5 and FIG. 6, a schematic diagram showing a use according to the present invention and a cross sectional schematic diagram showing a use state according to the present invention, respectively.

As shown, when the present invention is implemented, also referring to FIG. 1 through FIG. 4, a subject medicine 3 is combined with the bottom seat 11 of the case body 1. In combination, the medicine 3 is directly sleeved into a first sleeved area 111 or a second sleeved area 112 of the bottom seat 11 according to an outer diameter of a bottle body 31 receiving the medicine 3 therein. When the medicine 3 is sleeved into the first sleeved area 111 or the second sleeve area 112, a bottom face 11a of the bottom seat 11 or a joining area 11b of the first and second sleeved area 111, 112 is taken as a contact face with a rim of the bottle body 31. On the other side, lean-against portions 113, 114 on an inner rim of the first sleeved area 111 or the second sleeved area 112 lean against an outer rim of the bottle body 31, respectively. In this manner, between the medicine 3 and the bottom seat 11 exists a stably fixed state, so that a subsequent use is facilitated.

When the user is intent to take the medicine 3, he/she lays his/her thumb under the bottle body 31 and index finger and middle finger above the upper cap 11 of the case body 1, and puts a nozzle 32 in his/her mouth. Then, the user presses by exerting an axial force (with respect to the bottle body 31 with the thumb having a pressing direction opposite to that of the index finger and middle finger. At this time, the case body 1 transmits a pressure to the medicine 3, enabling the medicine to be spurted out from the nozzle 32. When the upper cap 11 of the case body 1 is forced to push the medicine 3, the resilient elements 13 are concurrently compressed, which causes the protruding rod 14 of the bottom seat 11 to move in an opposite direction and thus the protruding rod 14 gets in contact with the second triggering element, enabling the count unit 22 to count and the displaying unit 26 to display an increment/decrement number value through the window hole 121 and the transparent cap plate 122. Then, the force exerted by the thumb, index finger and middle finger is removed, whereby finishing the counting operation. However, after the user releases the pressing force, the resilient elements 13 each have its elasticity restored, causing the second triggering element 24 and the protruding rod 14 of the bottom seat 11 to separate with each other in opposite directions, respectively, and thus the upper cap 12 is automatically restored to its original position. In this manner, the above described steps are repeated, and the user may know the current number value for the used medicine 3 and continue to generate an increment/decrement.

In addition, the present invention also provides the user with the functions of resetting, correcting and adjustability. In operation, the through hole 123 of the upper cap 12 is caused to directly or indirectly contact with the pressing button 25, enabling the pressing button 25 to contact with the first triggering element 23 and the count unit 22 to count. Finally, the displaying unit 26 is directed to display the count result. At this time, the count information in use is displayed and the count number value may be additionally reset, corrected and adjusted by repeatedly triggering the first triggering element 23.

In view of the above, the medicine box counter may effectively improve the problems associated with the prior art, by directly combining the medicine and the bottom seat so that the resilient elements may be indirectly extruded when the user exerts a pressure upon the upper cap in the course of use and thus the bottom seat triggers the count mechanism to count, and by automatically restoring the upper cap to its original position by means of the resilient elements. Correspondingly, the advantages of rapid assembly, convenient use, effective medicine-taken counting/tracking and reduced manufacturing cost are provided.

The above are merely examples and preferred embodiments of the present invention, and do not limit the present invention. Any modifications and changes without departing from the scope of the spirit of the present invention are deemed as within the scope of the present invention. The scope of the present invention is to be interpreted with the scope as defined in the claims which follow.

What is claimed is:

1. A medicine box counter, comprising:
   a case body, comprising a bottom seat, an upper cap movably combined with the case body, and a plurality of resilient elements disposed between the bottom seat and the upper cap; and
   a count mechanism, disposed between the bottom seat and the upper cap, drivable by a compression course between the upper cap and the bottom seat to count, the compression force between the upper cap and bottom seat being recoverable to an original course by the plurality of resilient elements;
   wherein the bottom seat has a first face having a protruding rod disposed thereon and movably contacting the count mechanism and a second face having a first sleeved area and a second sleeved area communicatively connected to each other and having a step difference there between;
   the upper cap has a first face having a window hole thereon and a second face having a transparent cap plate enclosed thereon, and a through hole corresponding to the count mechanism is disposed at a position neighboring to the window hole; and
   the count mechanism comprises a fixation seat, a count unit fixed on the fixation seat and having a first face and a second face, a first triggering element disposed on the first face of the count unit, a second triggering unit disposed on the second face of the count unit and corresponding to the protruding rod, a pressing button corresponding to the protruding hole and the first triggering element, a displaying unit connected to the count unit and corresponding to the window hole, and a power unit connected to the count unit, wherein the resilient elements are disposed between the bottom seat and the fixation seat.

2. The medicine box counter as claimed in claim 1, wherein the first and second sleeved areas each have an inner rim having a plurality of lean-against portions disposed thereon.

3. The medicine box counter as claimed in claim 1, wherein each of the resilient elements is made of one of silicon glue and polydimethylsiloxane (PDMS).

4. The medicine box counter as claimed in claim 3, wherein each of the resilient elements has a hardness adjustable on demand.

5. The medicine box counter as claimed in claim 1, wherein the protruding rod is electrically conductive and drives the second triggering element to operate.

* * * * *